US012758452B2

(12) United States Patent
Srinivasan

(10) Patent No.: US 12,758,452 B2
(45) Date of Patent: Oct. 13, 2026

(54) ADVANCED MRI INCUBATOR HYBRID SYSTEM FOR SAFE INFANT IMAGING

(71) Applicant: Advanced Imaging Research, Inc., Cleveland, OH (US)

(72) Inventor: Ravi Srinivasan, Beachwood, OH (US)

(73) Assignee: Advanced Imaging Research, Inc., Cleveland, OH (US)

(*) Notice: Subject to any disclaimer, the term of this patent is extended or adjusted under 35 U.S.C. 154(b) by 0 days.

(21) Appl. No.: 18/862,762

(22) PCT Filed: May 20, 2022

(86) PCT No.: PCT/US2022/030170
§ 371 (c)(1),
(2) Date: Nov. 4, 2024

(87) PCT Pub. No.: WO2023/224631
PCT Pub. Date: Nov. 23, 2023

(65) Prior Publication Data

US 2025/0288477 A1 Sep. 18, 2025

(51) Int. Cl.
*A61B 5/055* (2006.01)
*A61B 5/00* (2006.01)
*A61G 11/00* (2006.01)

(52) U.S. Cl.
CPC ............ *A61G 11/007* (2013.01); *A61B 5/055* (2013.01); *A61B 5/704* (2013.01); *A61G 11/001* (2013.01); *A61B 2503/045* (2013.01)

(58) Field of Classification Search
None
See application file for complete search history.

(56) References Cited

U.S. PATENT DOCUMENTS

| | | | |
|---|---|---|---|
| 2005/0113668 A1 | 5/2005 | Srinivasan | |
| 2013/0150656 A1 | 6/2013 | Falk et al. | |
| 2016/0054404 A1* | 2/2016 | Duensing ............. | G01R 33/341 324/309 |
| 2019/0328596 A1 | 10/2019 | Rapoport et al. | |
| 2021/0156936 A1* | 5/2021 | Popescu ........... | G01R 33/34053 |

FOREIGN PATENT DOCUMENTS

CN 106580608 A 4/2017

OTHER PUBLICATIONS

International Search Report from corresponding International Patent Application No. PCT/US2022/030170 dated Jan. 12, 2023.
Written Opinion of the International Searching Authority from corresponding International Patent Application No. PCT/US2022/030170 dated Jan. 12, 2023.

* cited by examiner

*Primary Examiner* — Shahdeep Mohammed
(74) *Attorney, Agent, or Firm* — Renner, Otto, Boisselle & Sklar, LLP

(57) ABSTRACT

An incubator includes a patient compartment, a support structure, a patient table coupled to the support structure, an RF coil selectively coupled to the support structure, the RF coil including a receiver arranged along a peripheral edge of the RF coil, and a hood selectively coupled to one of the support structure or the patient table and configured to engage the receiver. When the hood is engaged with the receiver a volume of the hood and a volume of the RF coil merge together.

20 Claims, 6 Drawing Sheets

SNR COMPARISONS FOR A 4-ch R-ONLY SURFACE COILS AT 293K AND 88K

| Ax SE, 5mm slice thk, TR 800, TE 30, FOV 24cm, 128x256 matrix, L-R PE, 1 acq, 1:54 | 1.5T (64 MHz) | | | 3T (123.2 MHz) | | |
|---|---|---|---|---|---|---|
| | S | N | SNR | S | N | SNR |
| ROOM TEMP (293K) | 640 | 0.36 | 1779 | 1310 | 0.79 | 1658 |
| SUPER COOLED (88K) | 797 | 0.32 | 2491 | 1600 | 0.71 | 2254 |
| IMPROVEMENTS % | 25% | -11% | 40% | 22% | -10% | 36% |

ADVANCED MRI INCUBATOR HYBRID SYSTEM FOR SAFE INFANT IMAGING

TECHNICAL FIELD

The present invention relates to incubators for use in magnetic resonance imaging (MRI) and, more particularly, to a hybrid pediatric incubator and a radiofrequency (RF) coil system in which a volume of the RF coil and a volume of the incubator hood merge into a common volume and define an outer surface of the incubator.

BACKGROUND ART

Premature birth continues to be a leading cause of neonatal mortality in the US. Approximately 12% of all newborns are premature, and premature birth affects about 15 million infants in the US. Infants that are born premature are more likely to experience medical conditions, including impaired senses, breathing difficulties, and feeding difficulties, and may experience developmental delays. Additionally, preterm and low birth weight (LBW) infants weighing less than 2.5 Kg are at increased risk for hypothermia and vital-sign instability. In addition, many of these infants require respiratory support and intravenous infusions to support homeostasis. Effective diagnosis and monitoring of premature infants can help manage these issues as the infant grows.

MRI can help to predict clinical outcomes and thus is beneficial for neonatal cardiovascular and neurological evaluation. High field (3T) clinical systems with strong gradients (80 mT/m strength, 200 T/m/s slew rate) that provide increased signal-to-noise ratio (SNR) can support functional investigations beyond structural MRI. A 3T MRI system along with infant-sized radiofrequency (RF) coils attaining the needed temporal-spatial image resolutions in 30-45 minute can aid radiologists and researchers to delineate healthy versus diseased tissue and estimate functional connectivity. For example, reports of abnormal brain MRI at term ages strongly predicted adverse developmental outcomes. These reports suggest a role for early MRI as a risk stratification tool for childhood cognitive and academic impairment.

Delayed MR exams after infants regain stability can allow injuries to manifest, with very little room for timely intervention. In addition, minimal handling and transport of such infants is highly desired by trained NICU staff. That said, conventional incubators otherwise available in the NICUs are unsuitable for MRI, thereby demanding a custom solution.

Infants scanned without an incubator often become hypothermic, which is deleterious to health. Comparatively, infants scanned with adult-sized RF coils have compromised MRI SNR. This is due to low filling factors (anatomy vs. coil volume). To prevent signal aliasing, large imaging field-of-views (FOVs) are used, which result in sub-optimal image quality that can obscure diagnosis. In addition, the loud MRI noise (80-120 dBA) startle the resting infant resulting in unintended wake motion. To counter this, neonates are sedated at times, which can affect brain growth and development.

MRI incubator benefits include increased neonate access to MRI, neonates do not require sedation, reduced motion artifacts from 73% to 44%, etc. Conventional neonatal incubators designed per the international standard for stationary (IEC 60601-2-19) and transport incubators (IEC 60601-2-20) are focused on maintaining a high degree of air temperature uniformity in the patient compartment and, as a result, are relatively large. Conventional circulatory air paths that circulate air in the foot-head direction above the subject with the heater below the patient bed as commonly found in most incubators attempt to maintain heat uniformity over sensors spread evenly along the patient compartment. The sensors are used to measure uniformity of air temperatures 10 cm above the infant mattress. These large incubators are burdensome to warmup, operate, maintain, disinfect and service. Warmup time can take 30 minutes to 1.5 hours before the infant is introduced. No efforts are made to minimize user burden with fewer parts or to speed the pre-warming of air temperatures in the patient compartment (pre-warm or warmup). Further, due to the presence of ferromagnetic materials and the heater design, traditional incubators found in the intensive care units (ICUs) are not MR safe.

The lengthy 1-hour pre-warming and arduous routines (operation, disinfection, service, etc.) require additional staff hiring and pose substantial financial burden on the NICUs. The decade-old incubators require constant maintenance and updates, are expensive, and are limited to only research hospitals.

Distinct custom incubator and infant head/body coils can exacerbate user financial and operational strain. Since conventional RF coils are not part of the incubator, they typically are at room temperature and when inserted into the pre-warmed patient compartment, the temperature inside the incubator dips due to the relatively cold coil. Further, replacing head coils with body coils to perform cardiac exams requires patient movement, which disturbs the infant.

In summary, current devices pose excessive logistical complications during use (pre-warm, maintenance and service). Therefore, there is a need in the art for a less burdensome, simple, low-cost solution to facilitate safe transport and effective MRI in infants.

SUMMARY OF INVENTION

Conventional MRI rooms are maintained at lower temperatures than other areas of a medical facility to prevent patient core body temperature from increasing above the FDA allowable 1° C. limit. This may be suitable for adults, but not tolerated well by neonates and small babies and therefore the use of infant warming therapy is utilized to sustain life. An unmet need to simplify the means to enhance infant transport safety and facilitate effective MRI by improving the imaging resolution in small-anatomy subjects is essential. Otherwise, the arduous effort involved with transport is mitigated with low quality imaging data resulting in poor follow-up and/or clinical intervention.

In accordance with the invention, part of a volume of an incubator patient compartment is merged with part of a volume of an imaging coil to minimize the overall volume to be heated, which enables air temperature-rise within the incubator patient compartment to be extremely fast. More particularly, the imaging coil forms part of the outer structure of the incubator and also defines at least part of the inner surfaces of the patient compartment that are isolated from the external environment, i.e., the RF coil, along with an incubator hood and other components, define the volume of the isolated patient compartment. In this regard, the hood of the incubator is movable to engage and/or connect to a portion of the imaging coil, whereby the patient compartment is defined by surfaces of both the imaging coil and the hood.

The imaging coil can be compatible with parallel imaging techniques and multi-band imaging techniques. For example, the imaging coil can be formed as a massively parallel, multi-band imaging 32ch (64 element) 3T coil array, which will provide 3 dB higher SNR over conventional coils. By combining/merging the incubator volume with the imaging coil, a compact low-parts-count incubator design can be achieved that has optimal incubator-MRI performance with very fast warmup times (e.g., ≤10 minutes).

The system can include room temperature and/or supercooled "infant cocoons" with 3±0.5 dB and 6±1 dB SNR enhancements over commercial adult coils to obtain the highest image quality for a small anatomy. Additionally, MRI acoustic noise can be attenuated by 31-35 dBA, so infants can be scanned without sedation. The system utilizes a modular design to allow rapid warmup, disinfection, service, and simple operation.

According to one aspect of the invention, an incubator having a patient compartment includes: a support structure; a patient table connected to the support structure; an RF coil selectively coupled to the support structure, the RF coil including a receiver arranged along a peripheral edge of the RF coil; and a hood selectively coupled to one of the support structure or the patient table and configured to engage the receiver, wherein when the hood is engaged with the receiver a volume of the hood and a volume of the RF coil merge together.

In one embodiment, when the hood is engaged with the receiver an exterior surface of the patient compartment is defined by both the hood and the RF coil.

In one embodiment, when the hood is engaged with the receiver the RF coil forms an exterior surface of the incubator and an interior surface of the patient compartment.

In one embodiment, the RF coil is movably coupled to the support structure or the hood is movably coupled to the support structure or the patient table.

In one embodiment, the RF coil and the hood define an inner surface of the patient compartment.

In one embodiment, the RF coil forms part of an external superior incubator section.

In one embodiment, the incubator includes a height-adjusting device configured to adjust an elevation of the hood relative to the patient table.

In one embodiment, the receiver comprises a groove formed along an outer peripheral edge of the RF coil.

In one embodiment, the receiver comprises at least two right-angled surfaces that present at least three right-angled paths into and out of the patient compartment.

In one embodiment, the incubator includes a heater fluidically coupled to the patient compartment and operative to provide heated air into the patient compartment.

In one embodiment, the incubator includes an anterior cardiac/body RF coil arranged over the patient table, the cardiac/body RF coil movable relative to the patient table in elevation.

According to another aspect of the invention, an incubator having a patient compartment includes: a support structure; a patient table connected to the support structure; an RF coil selectively coupled to the support structure, the RF coil including a receiver arranged along a peripheral edge of the RF coil; and a hood selectively coupled to one of the support structure or the patient table and configured to engage the receiver, wherein when the hood is engaged with the receiver an exterior surface of the patient compartment is defined by both the hood and the RF coil.

According to yet another aspect of the invention, an incubator having a patient compartment, includes: a support structure; a patient table connected to the support structure; an RF coil selectively coupled to the support structure, the RF coil including a receiver arranged along a peripheral edge of the RF coil; and a hood selectively coupled to one of the support structure or the patient table and configured to engage the receiver, wherein when the hood is engaged with the receiver the RF coil forms an exterior surface of the incubator and an interior surface of the patient compartment.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

In the annexed drawings, like references indicate like parts or features.

FIG. 3A shows the hood in the open position and FIG. 3B shows the hood in the closed position.

DETAILED DESCRIPTION OF INVENTION

Figure 1:
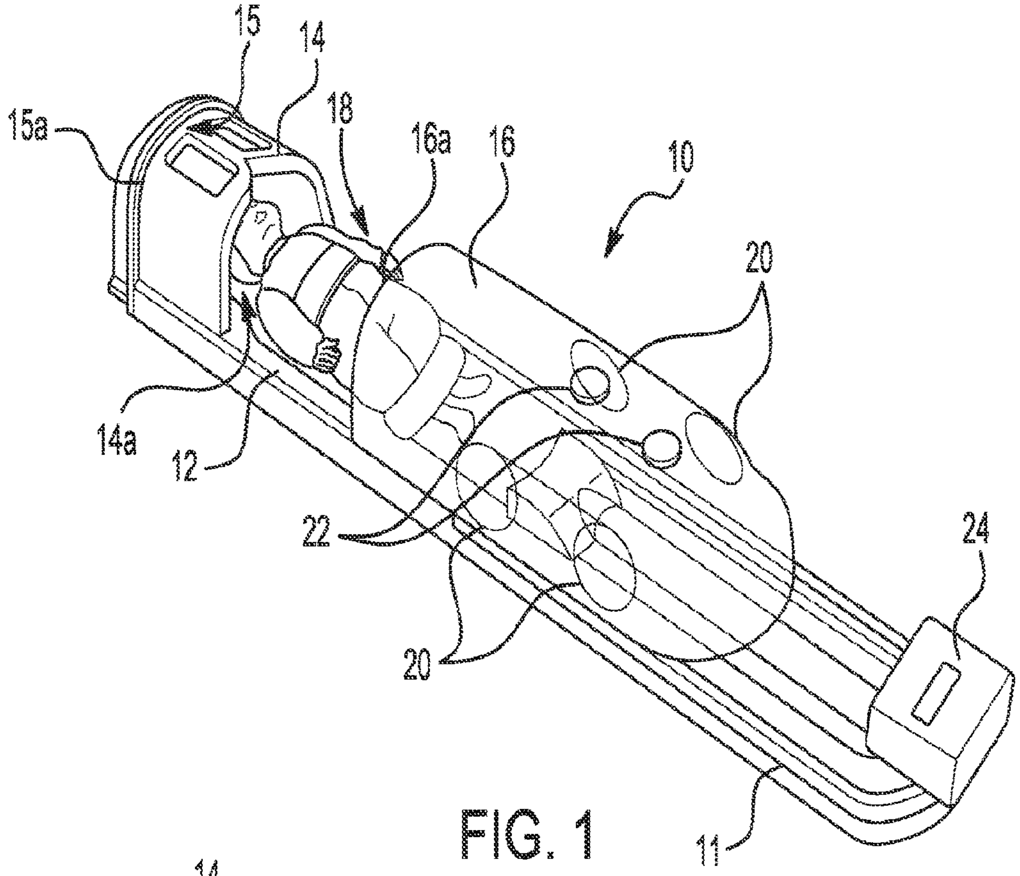
FIG. 1 is a perspective view of an exemplary incubator in accordance with the invention showing the infant head-spine array, the incubator having the hood in the open position.

Embodiments of the present invention will now be described with reference to the drawings. It will be understood that the figures are not necessarily to scale.

The term "hybrid" as used herein refers to two different components that perform essentially the same function. For example, and as discussed in further detail below, the hybrid incubator system in accordance with the invention has an RF coil array and an incubator hood that, in combination, define internal and external surfaces of a sealed patient compartment of the incubator.

Disclosed herein is a patient-centric, compact, hybrid incubator system that has fewer parts and includes a highly efficient, easy to use MR conditional incubator so infants can maintain "euthermia". The system can include room temperature and supercooled 'infant cocoons' with 3±0.5 dB and 6±1 dB SNR enhancements over commercial adult coils used to obtain the highest image quality on small anatomy. A means to attenuate MRI acoustic noises by 31-35 dBA can also be provided to enable infants to be scanned without sedation. Further, a modular design allows rapid warmup, disinfection, and service, with simple operation.

A compact, low-cost incubator in accordance with the invention is designed to accomplish fast 12° C. rise times per the IEC 60601-2-20 standard, in less than ten minutes and reach maximum incubator temperature of 39° C. in twenty minutes. Imaging goals between 0.5 L and 1 μL isotropic voxels over the neonatal brain and heart, respectively, in 15-20 minutes/each are obtainable. Enhanced image quality obtained with advanced RF coils can help unravel infant development and repair associated with a variety of neurological, psychiatric, neurodegenerative diseases, as well as those born with complex congenital heart and other disorders.

In accordance with the invention, size and heater power requirements of an incubator can be optimized by controlling the incubator volume and mass. More particularly, by merging the volumes of a portion of the incubator patient compartment with a portion of the imaging coil, the size and mass of the portions to be heated are substantially reduced. In merging the volumes, a portion of the incubator hood slides into a receiver, such as a groove or the like, on the RF coil, whereby both the RF coil and the hood define both an inner and an outer surface of the patient compartment (e.g., an outer surface of the imaging coil and the hood defines an outer dimension of the incubator and/or patient compartment, and an inner dimension of the imaging coil defines at least part of the patient compartment inner dimensions).

Generally, reducing the size of traditional or predicate MRI incubator designs will compromise air temperature uniformity over the infant mattress. In the incubator according to the present invention, reducing the incubator size is accomplished without compromising incubator specifications dictated by IEC 60601-2-20, by maintaining uniformity of ±1.5° C., over the infant mattress. The sharing between the diagnostic RF coil and the pediatric incubator volume and enclosure minimizes the number of incubator parts and facilitates drastic volume reduction of the patient compartment that results in a smaller and lighter incubator, with fewer parts, that can be quickly heated to a desired temperature.

Further, a unique airflow distribution is provided in which air flows only over an infant mattress. This is in contrast to conventional incubator airflow that first flows below the mattress and then above the mattress (which minimizes the air used to warm the patient). The unique airflow distribution subjects the air to less incubator mass to heat relative to the conventional airflow that is both below and above the mattress. The unique airflow speeds up the heating process and also enables the heater power/size to be significantly smaller in comparison to traditional incubators and predicate MRI incubators. This unique airflow distribution can be accomplished with air vents at the foot end of the patient table or on the table lateral sides, or a combination of both in the incubator patient compartment. The reduced heater power size also leads to increased operational efficiency, and the size reduction will help to facilitate a compact heater with a single outer cover thereby also minimizing total incubator parts count.

Figure 2:
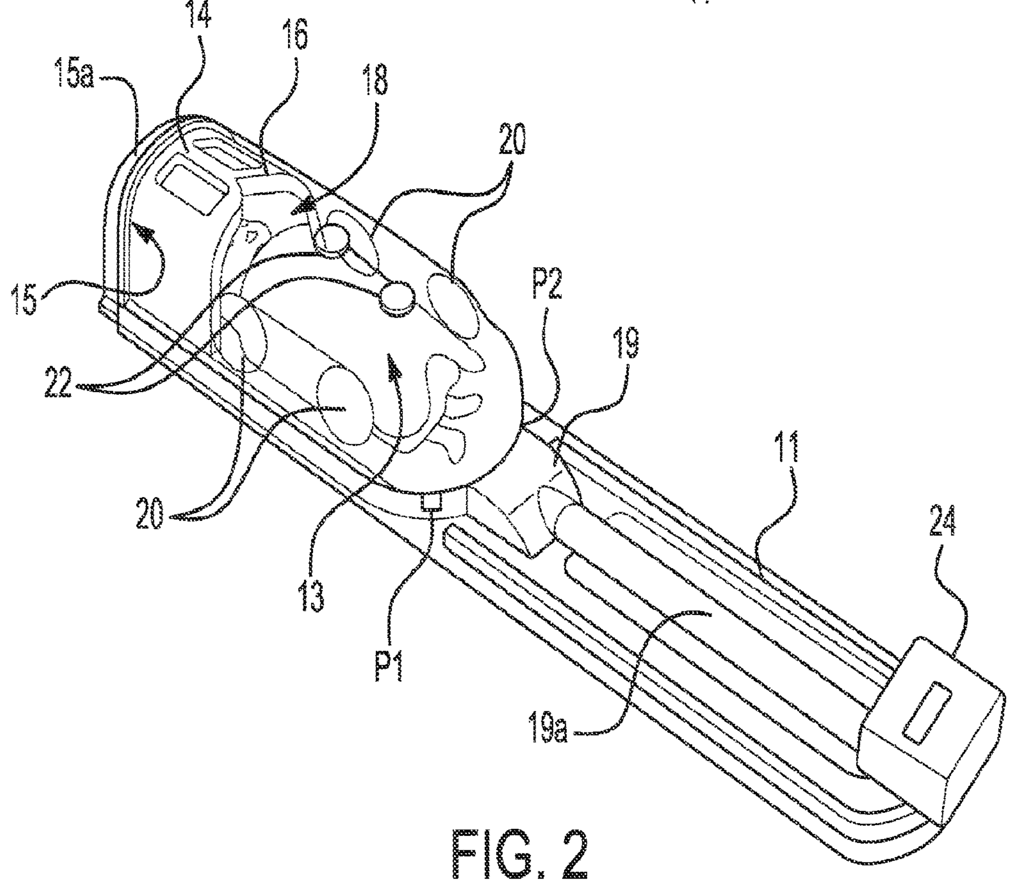
FIG. 2 is a perspective view of the incubator of FIG. 1 with the hood in the closed position and including an infant cocoon arranged over the infant.

Referring to FIGS. 1 and 2, illustrated is an exemplary incubator 10 in accordance with the present invention. The incubator 10 comprises a support structure 11 (e.g., a frame) and a patient support section 12 (also referred to as a patient table) on which an infant may be placed, the patent support section 12 attached to the support structure 11. An infant head-spine RF coil array 14 is attached to the support structure 11 and/or patient support section 12 and is optionally movable relative to the support structure 11 and patient support section 12. At least a portion of the RF coil array 14 (e.g., the head portion) is arranged over a portion of the patient support section 12 and another portion of the RF coil array (e.g., the spine portion) is arranged under or in the patient support section 12. The RF coil array 14 enables the infant's head and/or spine to be imaged during an MRI procedure. A movable clear hood 16 is connected to the incubator 10 and can be slidably positioned relative to the patient support section 12 and RF coil array 14 to open (FIG. 1) or close (FIG. 2) a patient compartment 18 of the incubator 10. When in the closed position, the internal incubator micro-environment within the patient compartment 18 is isolated from the ambient surroundings.

An "infant cocoon" is formed from a combination of the RF coil array 14 and an anterior cardiac/body section 13 for imaging the heart and major torso organs (such as kidney, spleen, liver, etc.) of the infant. As can be seen in FIGS. 1 and 2 (and further discussed below with respect to FIGS. 3A and 3B), a partial volume of the hood 16 (e.g., a leading edge of the hood 16*a* that interfaces with the RF coil) and a partial coil volume 14*a* merge, with the RF coil array 14 becoming part of the external superior incubator section (i.e., the RF coil array 14 forms an exterior surface of the incubator 10 and an interior surface of the patient compartment 18). The infant is supported by the patient support section 12, which may include a mattress pad (not shown) made with memory foam intended to enhance comfort and helps minimize imaging-vibration-related scanner motion artifacts. Immediate patient access is possible by simply moving the RF coil array 14 back to remove the coil from the support structure 11/patient support section 12 and/or sliding the anterior, single-piece incubator hood 16 towards the foot-side. As found in a conventional incubator, routine patient access can be via circular hand ports 20 on the incubator hood 16, which provide sealed access inside the incubator to preserve the incubator microenvironment. Life sustaining and vital sign monitoring equipment can be routed into the patient compartment 18 through ports P1 and P2.

In the illustrated embodiment of FIGS. 1 and 2, the support section 12 is positionally fixed in relation to the incubator patient compartment 18 and/or the support structure 11. A small heating section with a miniature heater 19 is also fixed to the support structure 11 and can be easily opened and cleaned with a single cover. Indirect, convectional air heating can be accomplished using one or more 24 VDC, ≤100 W, 8 mm dia., 40 mm long cylindrical cartridges (oriented in the head-to-foot direction), which may be inserted into respective power resistor holders and connected to the underside of a finned, 20 mm tall, 40 mm wide, ≤100 mm long aluminum heat sink. Fresh filtered air can be introduced into the patient compartment 18 and propelled via a duct 19*a* and motorized fan (not shown). The filtered air passes over a heated heat sink of the heater 19 alongside lateral sides of the infant to speed temperature rise-times while preserving air temperature uniformity of ≤1.5° C. per IEC 60601-2-20 standard, over the infant mattress in the patient volume 18.

With continued reference to FIGS. 1 and 2, two height-adjusting devices 22, e.g., turn-knobs 22, are arranged above the hood 16, the knobs 22 operative to adjust an elevation of the anterior cardiac/body section 13 relative to the patient support section 12. That is, by turning one or both 22 knobs the anterior cardiac/body section 13 can be brought closer or further away from the patient in the A-P (anterior-posterior) direction, i.e., adjustable in the A-P direction. Simply turning one-knob will tilt the anterior cardiac/body section 13 toward or away from the head or the feet. Additionally, two additional height adjusting turn knobs can be placed side-to-side (not shown) to facilitate left-right (L-R) tilt of the adjustable, anterior-posterior (A-P) positions. With the anterior cardiac/body section 13 closer to the anatomy, improved filling factors are possible and therefore better image quality can be achieved without putting pressure on the infant, thereby avoiding chest compression. Simply touching the infant's chest with the anterior cardiac/body section 13 during and/or moving the lines away from the anterior cardiac/body section surfaces will minimize or eliminate breathing related motion and blood-flow related MR susceptibility artifacts that can obscure the image.

The incubator of FIGS. 1 and 2 can be augmented with a sensor-feedback controlled PID heating algorithm and associated firmware configured to optimize the incubator heat-rise and air temperature uniformity over the patient supports section 12/infant mattress. Such sensor-feedback control can stably regulate the temperature to a set temperature (i.e., ≤1° C., at steady state), etc. per the transport incubator standard specifications IEC 60601-2-20. Two, MR safe fiber-optic skin sensors (for the sake of redundancy—not shown) can be used to monitor patient temperatures during NICU-MRI transport and during the MRI exam.

The hybrid incubator-coil embodiment of FIGS. 1 and 2 is easy to maintain, has minimal external components, and is easy to operate, maintain, satisfy hospital safety (IEC 60601-1) and infection control (biocompatibility ISO 10993, disinfection TIR-12) standards for medical equipment.

The RF coil array 14, which in the illustrated embodiment of FIGS. 1 and 2 is an infant head-spine coil array having unitary (one-piece) construction, can be slid below the MR patient support section 12 and detached from the support structure 11 without touching (or disturbing) the patient. The RF coil array 14 can include a receiver 15, such as a groove, slot or the like, along an outer peripheral surface that is shaped to cooperate and accommodate a leading edge 16*a* of the incubator hood 16, thereby closing the patient volume 18 to preserve and/or isolate the incubator microenvironment from the ambient environment. The receiver and/or hood 16 may include a gasket 15*a* to provide a seal between the hood 16 and the RF coil array 14 when the patient volume is closed.

Figure 3A:
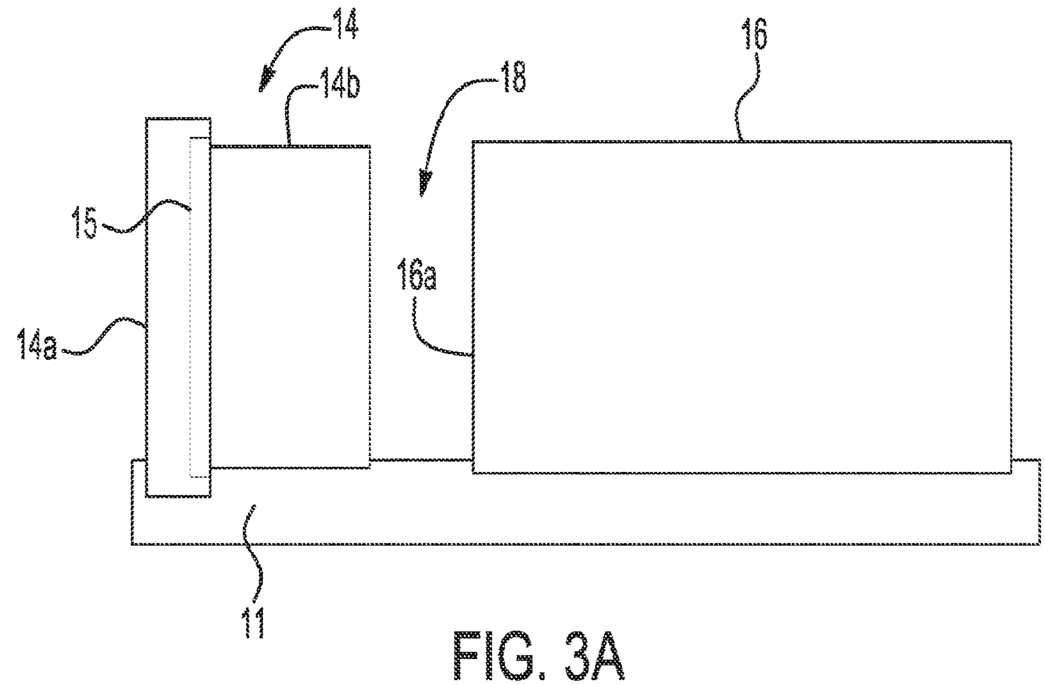
FIGS. 3A and 3B illustrate an RF coil of an incubator in accordance with the invention, the RF coil including a receiver for receiving a hood of the incubator, where
Figure 3B:
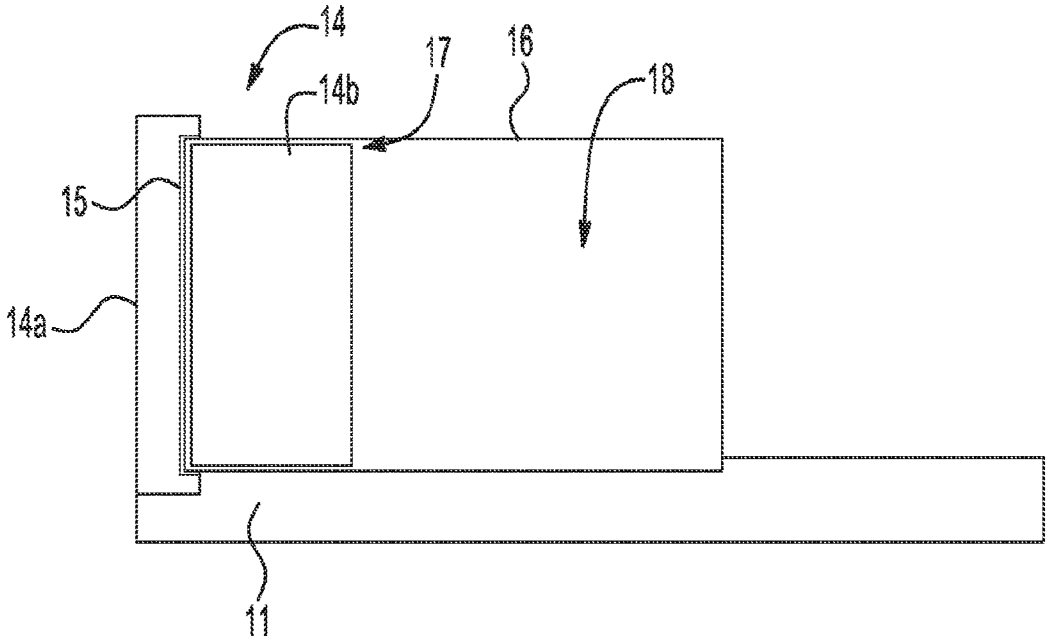

Referring briefly to FIGS. 3A and 3B, illustrated is an RF coil array 14 in accordance with the invention, the RF coil array 14 including a head portion 14*a* and an imaging portion 14*b*, wherein a receiver 15 is formed along a peripheral edge of the head portion 14*a*. The RF coil array 14 is movably attached to the support structure 11 and/or to the patient support section 12 to enable movement and/or detachment of the RF coil array 14 therefrom. A hood 16 is also movably attached to the support structure 11 and/or to the patient support section 12, the hood 16 movable between an open position (FIG. 3A) that provides access into the patient compartment 18 and a closed position (FIG. 3B) that seals the patient compartment from the outside environment. When the hood 16 is in the closed position, a leading edge 16*a* of the hood 16 engages with the receiver 15 of the RF coil array 14 to seal off the patient compartment from the outside environment. The receiver 15 may include a gasket 15*a* (see FIGS. 1 and 2) or other sealing member arranged along a surface of the receiver 15, where the hood engages the gasket to provide an airtight seal. Preferably, the hood 16 and RF coil array 14 are dimensioned such that there is a clearance fit between an inner surface of the hood 16 and an outer surface of the RF coil array 14. This clearance fit is illustrated in FIG. 3B by way of a gap 17, which is exaggerated for purposes of illustrating the clearance fit.

As best seen in FIG. 3B, when the hood 16 is engaged with the receiver 15 a volume of the hood 16 and a volume of the RF coil array 14 merge at the receiver 15 and/or at the imaging portion 14*b*. As a result, an exterior surface of the patient compartment 18 (i.e., an exterior surface in contact with the ambient air around the incubator and outside the patient compartment 18) is defined by exterior surfaces of both the hood 16 and the RF coil array 14. In this regard, the RF coil array 14 also forms part of an interior surface of the patient compartment 18, i.e., an inner surface of the RF coil array 14 defines part of the inner surface of the patient compartment 18.

In one embodiment the receiver 15 is shaped also to prevent the introduction of noise from the ambient environment (i.e., outside the incubator) into the patient compartment 16. For example, the receiver 15 may include a minimum of two right-angled surfaces to present a minimum of three right-angled paths that acoustic noises must travel in and out of the patient compartment 16. Further details of such right-angle configuration are discussed below with respect to FIG. 9. The RF coil array 14 shown in this embodiment can be removed and replaced with an identical "dummy" superior piece with the same inner curvature, such that the incubator can function without the coil, in extreme cases, but without any performance deviation.

A transport and MRI conditional neonatal ventilator 24 (see FIGS. 1 and 2) can be attached to the support structure 11 at an end distal from the RF coil array 14. By placing the ventilator 24 at the end distal from the RF coil array 14, ventilator perturbation to the MRI scanner can be reduced. More particular, the ventilator 24 functions properly even when placed at the middle of a 3T MRI scanner (i.e., at 3T field strength in the magnet center). The reason for its location in the preferred embodiment is to minimize the ventilator metal housing interaction with the whole-body gradients of the horizontal bore, superconducting magnet-based MRI scanners.

Since the RF coil array 14 forms part of the incubator housing and is present during warmup of the patient compartment 16, the air temperature in the patient compartment 16 can be quickly raised and can remain stable. This is in contrast to a conventional incubator, where a relatively cold RF coil is inserted into an already warmed (i.e., at the desired temperature) patient compartment, the relatively "cold" RF coil causing a temperature drop in the patient compartment 16.

Figure 4A:
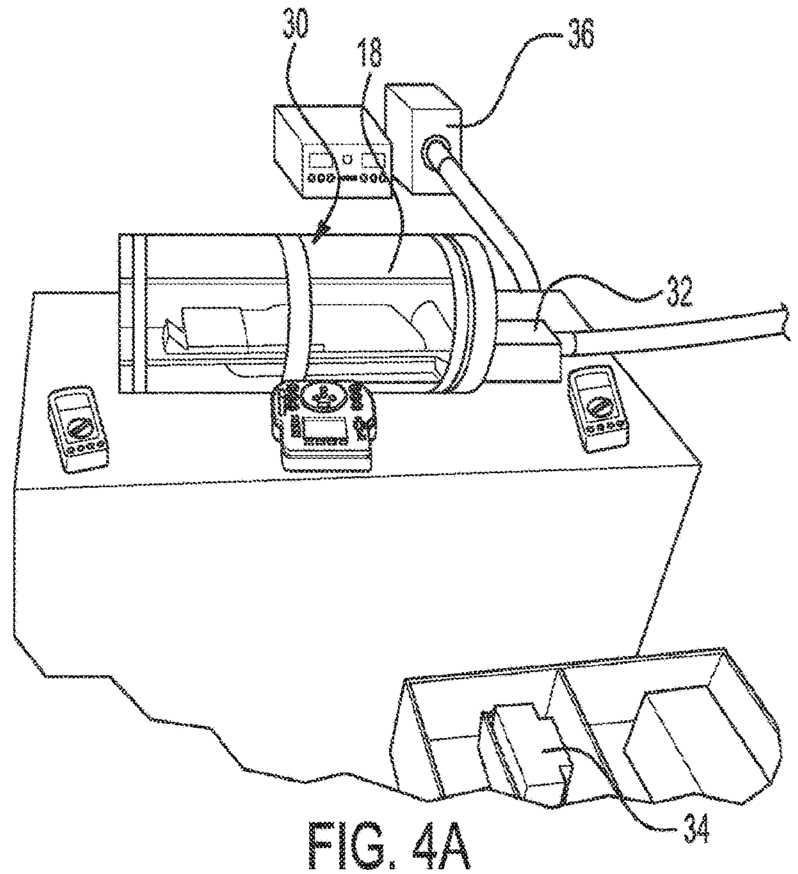
FIG. 4A illustrates a test configuration of an exemplary incubator in accordance with the invention.

With reference to FIG. 4A, illustrated is an MRI-compatible cylindrical incubator 30 capable of rapid air temperature rise-times in accordance with an embodiment of the invention. The incubator of FIG. 4A includes a ⅛" thick. polycarbonate, miniaturized heater 32 powered by either a single 24V, 40 AH battery 34 that can support 3 hour operation or by 120/230 VAC for continuous operation. A 12 VDC fan blower 36 moves filtered air over the heater and into the patient compartment 38. Indirect, convectional air heating is accomplished with two 24 VDC, 100 W, 8 mm dia., 40 mm long cylindrical cartridges (oriented Head to foot, configured in series/parallel depending on the desired power levels (low, medium, high) and heating modes) inserted within four power resistor holders and connected to the underside of a finned aluminum heat sink (see FIG. 6). By maintaining the air path traversing the heater fins above a bottom surface of the patient compartment 18, maintaining the heating section close to the patient compartment 18, and meandering heated air over the patient bed in the patient compartment 18, uniform heating per IEC 60601-2-20 standard can be obtained. With appropriate choice of the heater size, heating power, volume, and air transit speed over the heater and employing smart feedback-sensor based PID algorithms, one can accomplish swift and even heating over the patient compartment.

Figure 4B:
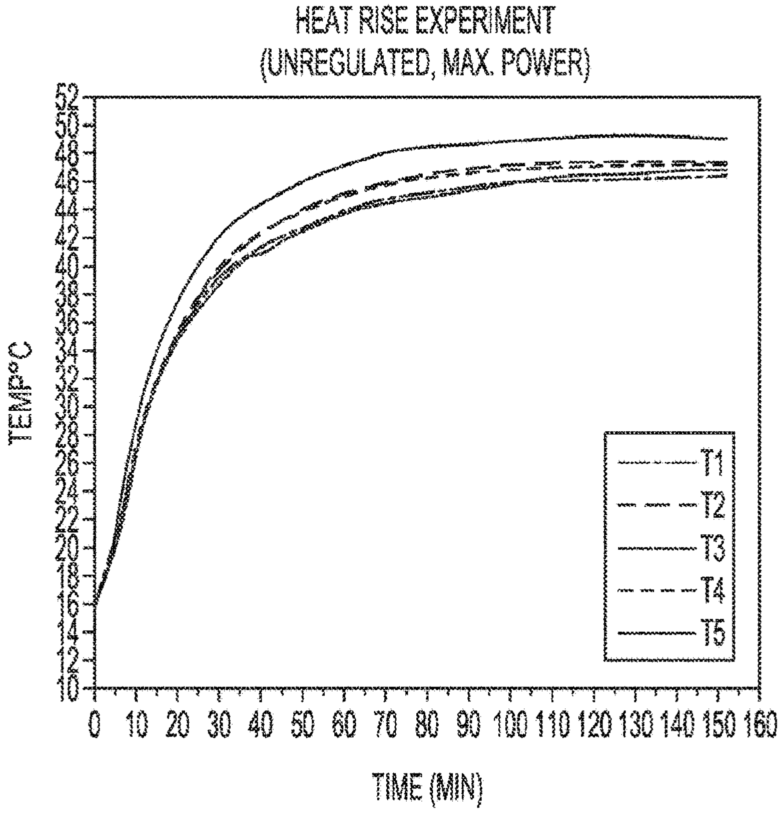
FIG. 4B is a graph showing heat rise over time for the incubator of FIG. 4A.

With a continuous, fresh-filtered air supply of 8 CFM, rapid heat-rise is possible as illustrated in FIG. 4B (which corresponds to the cylindrical embodiment of FIG. 4A). A 12° C. air temperature rise was achieved in the fastest warmup time of 9.5 min. at 17.8° C. start ambient temperature, and to the maximum allowable 39° C. from a cold start in 20 min. at 17.8° C. ambient temperature, which is significantly faster than current commercial incubators. The inset on the bottom-left of FIG. 4A illustrates the 5-sensor locations (T1—superior left, T2—superior right, T3—inferior left, T4—inferior right, T5—Center), 10 cm above the patient bed per the IEC 60601-2-20 standard. Further, air temperature was higher in the central incubator sensor T5, which was expected owing to the cylindrical design forced air to the central volume. The most notable measurement was the air temperature deviation observed by the five probes (using the Fluke Biomedical's INCU II incubator tester) spread throughout the infant mattress of FIG. 4A. The deviation was 1.1° C. at 33° C. and ±1.23° C. at 39° C., respectively, and well within the international standard limits of ±1.5° C. per IEC/AAMI 60601-2-20 for transport incubators. That is, the temperature distribution of the incubator of FIG. 4A was uniform over the entire infant mattress, despite the rapid air temperature rise design. Additionally, the temperature remained consistent as the air temperature rose inside the incubator five minutes after cold start, as illustrated on FIG. 4B. These data reveal minimal temperature deviation for the incubator of FIG. 4A per the incubator standard specification.

Accordingly, the proposed incubator having a substantial reduction in patient compartment volume helps to economize the hybrid assembly with fewer parts, improves efficiency, and minimizes customer burden with use and maintenance.

Figure 5:
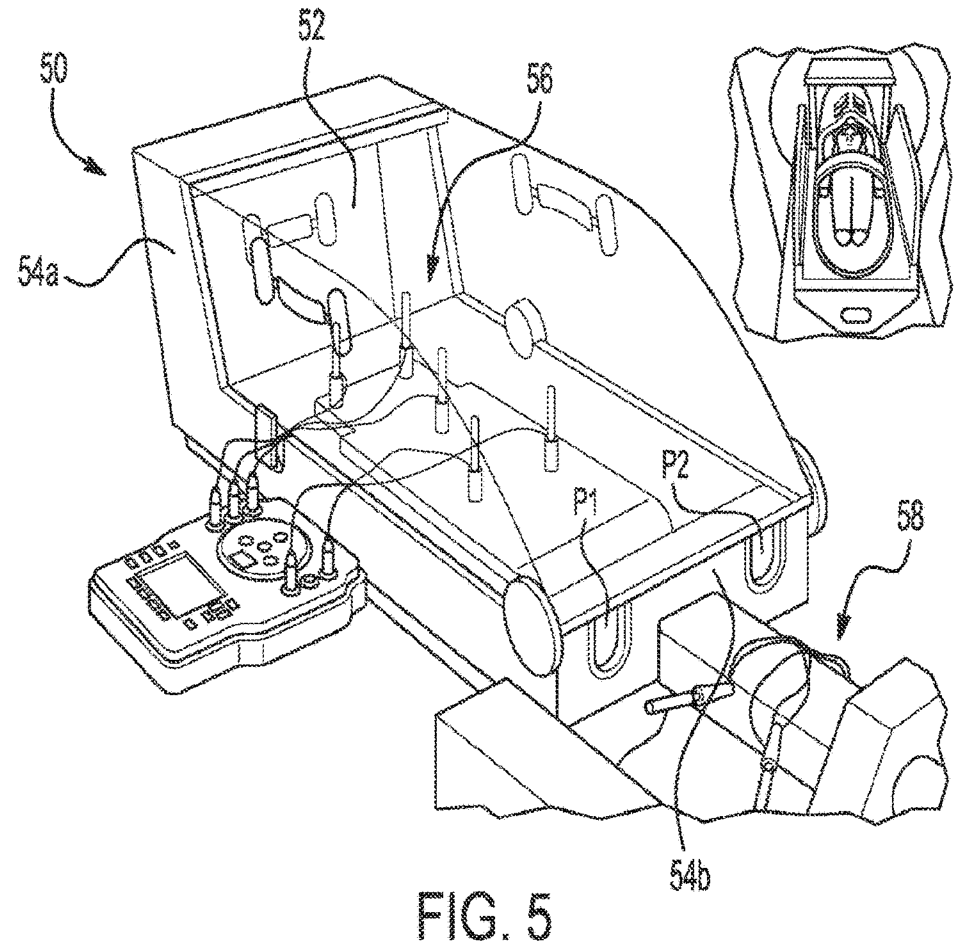
FIG. 5 illustrates a test configuration of another exemplary incubator in accordance with the invention.

With reference to FIG. 5, illustrated is another incubator 50 in accordance with an embodiment of the invention. The embodiment of FIG. 5 employs an efficient design that provides a short air path and reduced incubator material (volume and mass). The incubator 50 of FIG. 5 uses less heater power than the embodiment of FIG. 4A while providing swift air temperature rises. A 11" W×11 H×30" L patient compartment incubator shell 52, with a small (1.5"×1.6") heating cross-section is shown.

A single heater is shown outside of the patient compartment in the embodiment of FIG. 5 (as well as in the embodiment of FIG. 4*a*). It is noted that more than one heater can be utilized in each embodiment. Also, the heater can be located inside, partially inside or completely outside the patient compartment.

The 22" long mattress 54 (patient bed) is sufficient to accommodate a 55 cm long infant (see inset). The incubator hood volume merges with the RF coil array volume to define the patient compartment, thereby minimizing the volume to be heated and enabling use of reduced heater power/size. As used herein, merging of the volumes means that a volume of the hood and a volume of the coil come together to form a new shared volume that includes parts of each of the hood and the coil (the volume is enclosed and defined by both the coil and the hood).

Figure 6:
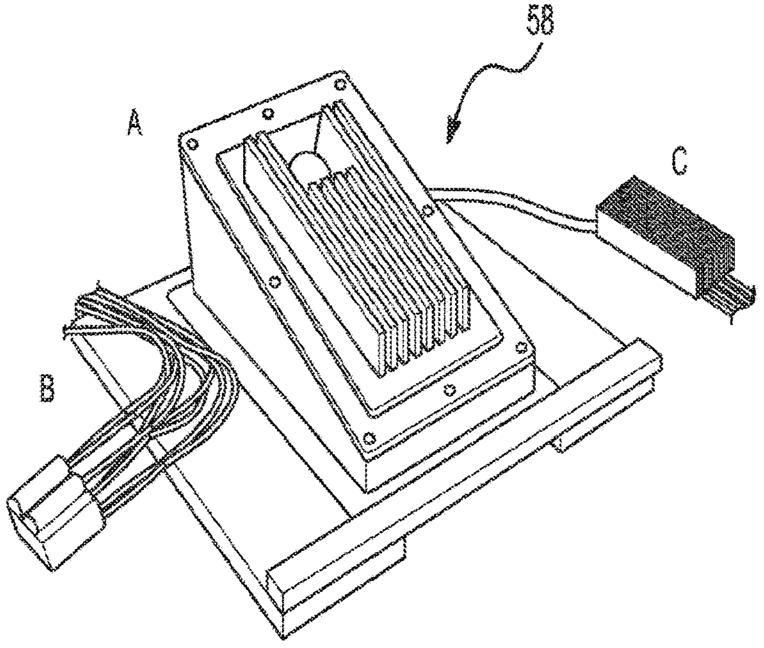
FIG. 6. Illustrates three different heating elements, where element A is a conventional heating element, element B is an advanced heating element having multiple heaters on top and bottom sides of a finned element, and element C is a variation of element B with heating elements on one side of the finned element.

Removable anterior/superior sections 54*a*, 54*b* provide immediate access to the patient compartment 56. Ports (P1, P2) enable the infant to be connected to the vital sign equipment (not shown). An RF coil insert (not shown in FIG. 5) can replace the superior incubator section 54*a*. A heating section 58 houses the heater that heats air prior to entry into the patient compartment 52. The inset of FIG. 5 shows incubator-cocoon assembly with an infant inside the incubator. For this embodiment, two 8 mm outer diameter, 40 mm long tubular, 24 VDC 100 W heater cartridges and aluminum-finned heat sink at 1⁄10th of conventional incubator heater volume as illustrated in FIG. 6 is sufficient to surpass 12° C. air temperature rises in roughly 10 min. In testing the embodiment of FIG. 5, air temperatures rose from 18 to 39° C. in 20 min. and remained steady at approximately 46° C.

As seen in FIG. 6, the substantial physical size reduction of the heater 58 is combined with increased low-power heating efficiency. Heater element A is a conventional incubator heater having a large finned heat sink with heating elements (not shown) below the heat sink. Heater element B illustrates an improved device with multiple cartridge heaters arranged above and below a finned heat sink that is substantially smaller in size than the heat sink of element A. Element C is similar to heater element B but has cartridge heaters on a bottom side but not on a top side of the finned heat sink. The power component of the exemplary heater 58 utilizes a 20 mm tall, 40 mm wide, 100 mm long aluminum heat sink that is attached to a 200 W heater, with a blower providing 8 CFM airflow.

Figures 7, 8:
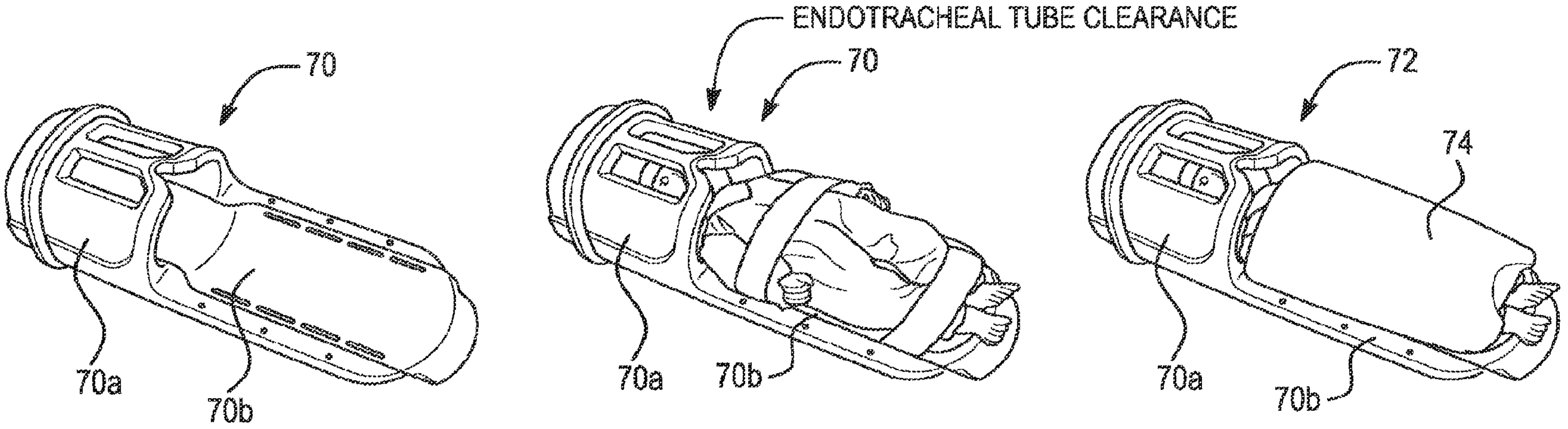
FIG. 7 is a perspective view of a 32ch (48 element) infant head-spine array (left and center) and 32ch (64 element) infant cocoon (right).
FIG. 8 is a table comparing signal-to-noise ratio for 4-ch Receive-only surface coils at 293K (25° C.) and 88K (−185° C.).

Moving now to FIG. 7, three-dimensional renderings of a thirty-two element head and sixteen element spine (forty-eight element total) that forms the infant head-spine coil array 70 (left and center images) and thirty-two channel (sixteen element-four element) infant cocoon 72 formed from an anterior cardiac/body section 74 arranged over the head-spine array 70 (right image) are illustrated. The infant head-spine array 70 and cocoon 72 are can be used in the incubator embodiments of FIGS. 1, 2, 3A, 3B, 4A and 5.

The exemplary infant head-spine coil array 70 includes thirty-two individual coil elements in the head section 70*a* and sixteen individual coil elements in the spine section 70*b*. Each individual coil in the array overlaps with the neighboring coils to maintain minimum mutual coil coupling necessary to lower the overall combined noise and maximize combined SNR of the coil array. The infant cocoon 72 is formed from a combination of the infant head-spine array 70 plus a sixteen element anterior cardiac/body section 74 that can be adjusted in the A-P direction in order to maximize SNR and minimize motion artifacts as explained above. Using a twenty channel infant cocoon (8-head, 8-spine, 4-anterior cardiac), 39% and 29.4% SNR improvements were obtained over a commercial thirty-two channel head coil on a 3T MRI. With greater number of channels and smaller receiver coils, SNR improvement of >3 dB (i.e., >40%) is achievable with room temperature infant sized coils over OEM adult counterparts. Owing to the smaller stature, the maximum allowable MR frequency without considering SAR and FDA limits for imaging infants (≤4T) is estimated to be around 300 MHz (7T) before approaching RF propagation artifacts.

The MRI coils of the arrays 72 and 74 can be built with 12-16 gauge Ag-coated copper wires to attain QunI/QI ratios between 4 and 8. A ratio <4 relating to a coil insensitive to the load (coil dominant) and a ratio >8 relating to a lossy sample (sample dominant), will affect optimum achievable coil SNR. MR transparent materials such as urethane, polycarbonate, nylon, or PVC are used to eliminate artifact introduction while satisfying safety (IEC 60601-1) and MR specific (IEC 60601-2-33) and hospital infection (biocompatibility ISO 10993, disinfection AAMI TIR-12) standards for class II medical devices. Outer XYZ coil dimensions are expected to be 10" H×10" W×27" L sufficient to cover 0-6 months old infants.

With reference now to FIG. 8, the benefits of increased signal and reduced noise can be seen in phantom and in-vivo experiments with receive-only coil arrays on 1.5T and 3T MRI scanners. For an eight-channel parallel plate receive 1.5T and 3T arrays (not shown), phantom experiments demonstrated 3±0.5 dB SNR benefits of super-cooling. Overall noise (N) reduced by 11% and 10%, whereas signal(S) increased by 25% and 22% resulting in SNR increases of 40% and 36% at 1.5T and 3T. Reduced noise factors can be attributed to very low coil Johnson-Nyquist thermal noise contributions at 88K. Signal increases were due to increased conduction currents. Together, they ($\downarrow$N, $\uparrow$S) concomitantly helped to enhance phantom SNR.

Figure 9:
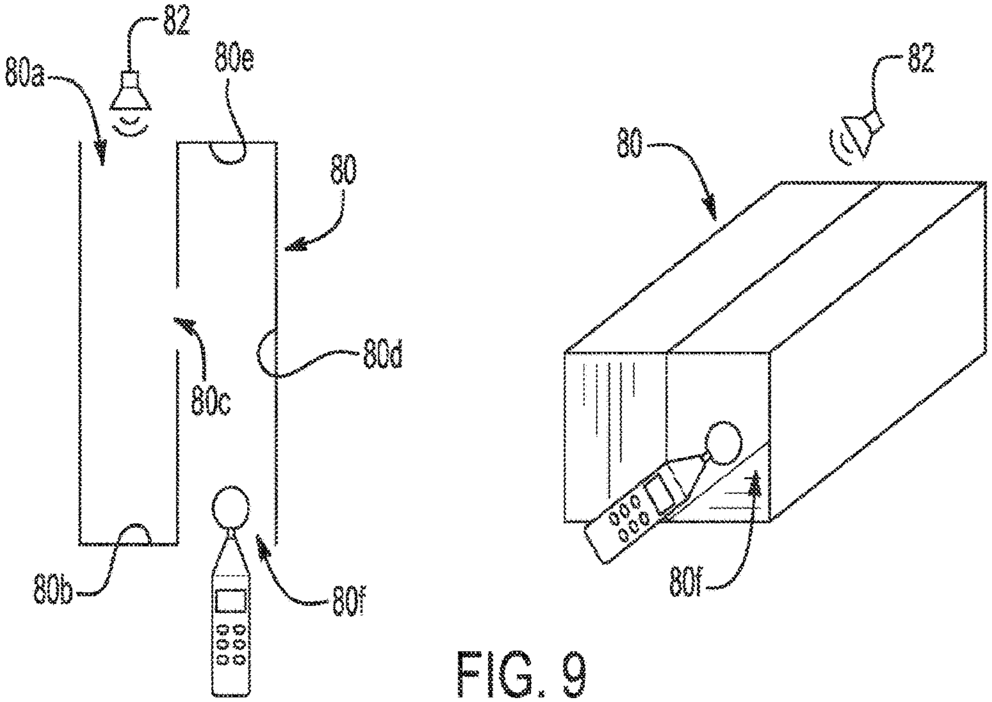
FIG. 9 illustrates an exemplary noise attenuating port extension that can be used to attenuate noise coupled into the incubator patient compartment.

With reference to FIG. 9, a two-section, four-sided, ⅛" thick walled closed incubator extension 80 that can be used with the receiver 15 of FIGS. 1-3B and/or the two ports P1, P2 of FIGS. 1 and 2 is shown relative to a noise source 82, which symbolizes noise generated by the MRI. A 12" long section, with 2"×2" cross-sectional ID and 1" opening between sections provides greater than 3 dB attenuation of acoustic noises in the range of 1-4 KHz, which is typical in MRI scanners. For example, noise from noise source 82 enters at port 80*a*, and some noise strikes wall 80*b* and is bounced back out of the port 80*a*, while some noise passes though the opening 80*c*. The noise passing through opening 80*c* strikes wall 80*d* and can bounce upward toward wall 80*e* and downward toward port 80*f*. Since only the sound waves manifesting at the port 80*f* are audible, the total sound at port 80*f* is significantly reduced relative to the noise entering port 80*a*. By adding a second extension 80, greater than 6 dB acoustic noise attenuation can be achieved, which is adequate to dampen the noise introduced through the receiver 15 and/or the ports P1, P2.

The noise introduced into these port extensions is a fraction of the noise generated by a 60 cm diameter magnet bore and estimated to be the ratio of the port extension opening area to the magnet bore cross-sectional area, causing the gradient induced eddy current noises in the 1-4 KHz range. For a 2"×2" port opening and for both ports the combined noise attenuation is estimated to be roughly 34.8 dB, which is close to the noise attenuation for the incubator hood. That is, for 105 dB noise levels generated by a 60 cm inner-diameter magnet bore MRI scanner, roughly 70 dBA, which is identical to soft-spoken noises in the NICU, will be felt inside the patient compartment. By adding the port extensions of FIG. 9 to the incubators of FIGS. 1 and 2, another 3-6 dB acoustic noise attenuation can be realized, for a total of 64-67 dB A-weighted noise levels reaching inside the patient compartment, which is acceptable. Because noise can creep into the patient compartment 18 affecting the infant, appropriate design precautions should be taken to go beyond that required for incubators and should consider the MRI aspects for incubator noise reductions. In particular, noise creeping into the patient compartment 18 other than just through the hood 16 and hand ports 20 should be considered for the MRI incubator. Also, since the infant is laying on the same level or slightly above the port openings in the patient compartment 18, care must be taken to route life sustaining tubes and vital signs monitoring lines while at the same time attenuating noise. Incubator size reduction generally works against noise attenuation with the noise sources coming closer to the infant in the patient compartment 18, making noise attenuation a significant design component of one embodiment of the incubator. Careful rounded hood transitions and avoidance of sharp edges and corners help to minimize noise resonances inside the patient compartment 18. Additions of noise dampeners in the form of cylinder protrusions outside the incubator hood 16 and/or the extensions 80 intended to upset the noise standing-wave at the audible frequencies can reduce noise in the patient compartment 18. The use of the noise dampening Natus minimuffs (7 dBA), custom pads (6 dBA), custom incubator design (20-22 dbA) and >3 dBA custom noise-attenuating ports connecting the baby to life sustaining equipment will help to provide 35±2 dbA acoustic noise attenuation needed to reduce the 105 dBA MRI noises to audible NICU noise levels of 70 dBA (soft spoken voice).

Figure 10:
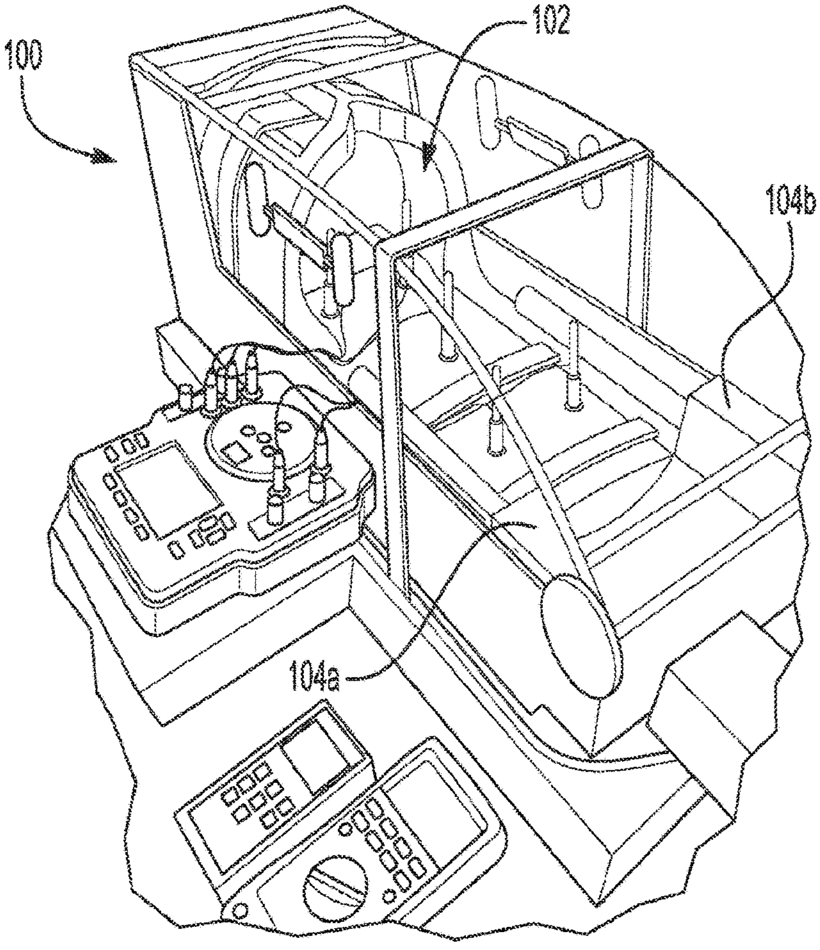
FIG. 10 illustrates another exemplary incubator in accordance with the invention.

Referring now to FIG. 10, illustrated is another exemplary incubator 100 in accordance with the invention. The incubator 100 of FIG. 10 is similar to the incubator 50 of FIG. 5 but includes multiple heaters arranged within the patient compartment 102. In particular, two heaters 104*a*, 104*b* are placed in the foot compartment of the patient compartment 102, one heater 104*a* on the left side and one heater 104*b* on the right side. Splitting the heat supply into two separate units arranged on opposite sides of the patient compartment 102 can accelerate temperature rise times in the patient compartment 102. For example, 12 degree C. rise times can be achieved within 5-7 minutes.

Design simplicity with distinct functions for individual sections affords modularity, which simplifies operation, maintenance, and service. For example, the heating section can be removed or heater cartridge and/or fuse replaced by authorized service technicians in 5-10 minutes, reducing the overall burden and service costs. The incubator, which preferably has minimal or no removable parts, can be cleaned and disinfected in 5-10 minutes plus the time allowable by the chemical agent to accomplish effective disinfection, which is substantially shorter than the one hour process with current MRI incubators with several removable parts.

With infant-sized room temperature coils 3±0.5 dB SNR improvement is anticipated, and with super-cooled coils another 3±0.5 dB SNR improvement is expected, for a total of 6±1 dB SNR improvement over commercial adult coils. Coils are engineered to survive the harsh incubator conditions and frigid temperatures alike, as mentioned above. Several means of supercooling can be employed to operate the coils at frigid temperatures <−130° C. (243° K). Likewise, choice of different coil design, materials and cooling mechanisms can be envisaged and may be feasible. Several short air paths in the patient compartment can be envisaged which enable swift air temperature rises in the patient compartment as measured per the international transport incubator standard (IEC 60601-2-20) without ≥±1.5° C. deviation (also per the same standard) necessary to maintain heat uniformity over the tiny subject. Several miniature heater and air heating designs are possible. Different sensor feed-back mechanisms and altered PID algorithms per air temperatures in and out of the incubator, including heater surface temperatures and ambient surrounding temperatures are feasible. Operating the incubator based on the air and baby skin temperature are feasible. Different noise dampening schemes by one skilled in the art are possible after reading this application.

An incubator-coil hybrid combination in accordance with the invention allows safe transport and effective diagnosis via MRI in infants seeking stat diagnosis and awaiting clinical intervention. Mass and volume are reduced to enable swift air temperature rises, with a fewer parts count, lightweight, low-cost, high performance, hybrid medical device suitable for infants.

A simpler incubator design with no ferromagnetic parts will be safe for use in an MRI scan room. Whereas a miniature DC heater (from 120/230 VAC to 24 VDC) will also be safe for use in the MRI scan room with less MR artifacts due to the absence of alternating current (AC) on a conducting wire inside a strong magnetic field. With minimal interferences to the steady strong magnetic field (magnet), rapid-switching alternate magnetic fields (gradients) and to the transmit RF of the whole-body coil, very little or no filtering is required. A miniature aluminum heater will present very little or no eddy currents and therefore also present a safe design to all magnetic fields, thereby allowing a single design to perform efficiently at all MRI field strengths without compromising incubator specifications.

With the compact, hybrid incubator system in accordance with the invention, safe transport and advanced stat diagnosis are possible, without the infant having to leave the incubator. Swift temperature rise times will expedite prewarm, while fewer incubator parts cut preparation times and considerably minimize the overall transport risk burden and enhance staff confidence. The incubator in accordance with the invention can reduce the large 400 W, 120/230 VAC heater-driven MRI conventional incubator with numerous parts to a subcompact, <200 W miniature 24 VDC heater-driven (i.e., ≥50% power reduction and ≥400% temperature rise times) version with fewer parts will help to reduce the size, use burden and cost. Converting the drive from AC power to DC power will help to minimize or eliminate eddy currents caused due to a varying current (hence varying electric field) in a static (steady) magnetic field (Lenz's law). The miniature heater will help to minimize magnetic eddy currents and displacement force while the MR patient table is moving in a magnetic field (i.e., during patient introduction and release from the imaging position inside the magnet bore). The miniature heater will also minimize gradient interactions to a metal object in or near its field-of-view (FOV) which can otherwise cause slice shifting due to eddy currents. The miniature heater will also minimize whole-body transmit RF interactions and increase localized SAR due to high electric fields over the heater and wires connecting to it, causing elevated SAR.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

What is claimed is:

1. An incubator of a magnetic resonance imaging (MRI) system including a patient compartment, comprising:

a support structure;

a patient table connected to the support structure;

a radiofrequency (RF) coil selectively coupled to the support structure, the RF coil including a receiver arranged along a peripheral edge of the RF coil; and a hood selectively coupled to one of the support structure or the patient table and configured to engage the receiver, wherein when the hood is engaged with the receiver a volume of the hood and a volume of the RF coil merge together;

wherein the MRI system is configured to generate acoustic noise from a noise source during operation, the noise source being exterior of the patient compartment;

wherein the receiver defines a bounded passage extending between an exterior of the patient compartment and an interior of the patient compartment, the passage including:

an entrance port opening from the exterior of the patient compartment into the receiver;

a first passage segment extending from the entrance port in a first direction;

a first reflective surface at an end of the first passage segment, the first reflective surface being orthogonal to the first passage segment;

a second passage segment joined to the first passage segment and extending in a second direction oriented at a right angle relative to the first direction;

a second reflective surface at an end of the second segment, the second reflective surface being orthogonal to the second passage segment;

a third passage segment joined to the second passage segment and extending in a third direction oriented at a right angle relative to the second direction; and an exit port opening from the third passage segment into the interior of the patient compartment;

wherein the first reflective surface and the second reflective surface are orthogonal to one another, and the first passage segment, the second passage segment, the first reflective surface, and the second reflective surface are structurally arranged such that acoustic waves entering through the entrance port and propagating along the first passage segment strike the first reflective surface, with a first portion of the acoustic waves reflected back toward the entrance port, and a second portion of the acoustic waves passing into the second passage segment and striking the second reflective surface, the second reflective surface reflecting the second portion back toward the first passage segment and away from the exit port;

whereby, by virtue of the structural arrangement, acoustic energy at the exit port is reduced relative to acoustic energy entering through the entrance port.

2. The incubator according to claim 1, wherein the RF coil is movably coupled to the support structure or the hood is movably coupled to the support structure or the patient table.

3. The incubator according to claim 1, wherein the RF coil and the hood define an inner surface of the patient compartment.

4. The incubator according to claim 1, wherein the RF coil forms part of an external superior incubator section.

5. The incubator according to claim 1, further comprising a height-adjusting device configured to adjust an elevation of the hood relative to the patient table.

6. The incubator according to claim 1, wherein the receiver comprises a groove formed along an outer peripheral edge of the RF coil.

7. The incubator according to claim 1, further comprising a heater fluidically coupled to the patient compartment and operative to provide heated air into the patient compartment.

8. The incubator according to claim 1, further comprising an anterior cardiac/body RF coil arranged over the patient table, the cardiac/body RF coil movable relative to the patient table in elevation.

9. The incubator according to claim 1, wherein when the hood is engaged with the receiver, the RF coil forms an exterior surface of the incubator and an interior surface of the patient compartment.

10. The incubator according to claim 1, wherein the entrance port and the exit port are laterally offset from one another such that acoustic waves entering through the entrance port traverse the orthogonal path segments before reaching the exit port.

11. An incubator of a magnetic resonance imaging (MRI) system including a patient compartment, comprising:
- a support structure;
- a patient table coupled to the support structure;
- a radiofrequency (RF) coil selectively coupled to the support structure, the RF coil including a receiver arranged along a peripheral edge of the RF coil; and
- a hood selectively coupled to one of the support structure or the patient table and configured to engage the receiver, wherein when the hood is engaged with the receiver, an exterior surface of the patient compartment is defined by both the hood and the RF coil;
- wherein the MRI system is configured to generate acoustic noise from a noise source during operation, the noise source being exterior of the patient compartment;
- wherein the receiver defines a bounded passage extending between an exterior of the patient compartment and an interior of the patient compartment, the passage including:
  - an entrance port opening from the exterior of the patient compartment into the receiver;
  - a first passage segment extending from the entrance port in a first direction;
  - a first reflective surface at an end of the first passage segment, the first reflective surface being orthogonal to the first passage segment;
  - a second passage segment joined to the first passage segment and extending in a second direction oriented at a right angle relative to the first direction;
  - a second reflective surface at an end of the second passage segment, the second reflective surface being orthogonal to the second passage segment;
  - a third passage segment joined to the second passage segment and extending in a third direction oriented at a right angle relative to the second direction; and
  - an exit port opening from the third passage segment into the interior of the patient compartment;
- wherein the first reflective surface and the second reflective surface are orthogonal to one another, and the first passage segment, the second passage segment, the first reflective surface, and the second reflective surface are structurally arranged such that acoustic waves entering through the entrance port and propagating along the first passage segment strike the first reflective surface, with a first portion of the acoustic waves reflected back toward the entrance port, and a second portion of the acoustic waves passing into the second passage segment and striking the second reflective surface, the second reflective surface reflecting the second portion back toward the first passage segment and away from the exit port;
- whereby, by virtue of the structural arrangement, acoustic energy at the exit port is reduced relative to acoustic energy entering through the entrance port.

12. The incubator according to claim 11, wherein the RF coil and the hood define an inner surface of the patient compartment.

13. The incubator according to claim 11, wherein the RF coil forms part of an external superior incubator section.

14. The incubator according to claim 11, further comprising a height-adjusting device configured to adjust an elevation of the hood relative to the patient table.

15. The incubator according to claim 11, wherein the receiver comprises a groove formed along an outer peripheral edge of the RF coil.

16. The incubator according to claim 11, wherein the receiver comprises at least two right-angled surfaces that present at least three right-angled paths into and out of the patient compartment.

17. The incubator according to claim 11, wherein when the hood is engaged with the receiver, the RF coil forms an exterior surface of the incubator and an interior surface of the patient compartment.

18. An incubator of a magnetic resonance imaging (MRI) system including a patient compartment, comprising
- a support structure;
- a patient table coupled to the support structure;
- a radiofrequency (RF) coil selectively coupled to the support structure, the RF coil including a receiver arranged along a peripheral edge of the RF coil; and
- a hood selectively coupled to one of the support structure or the patient table and configured to engage the receiver, wherein when the hood is engaged with the receiver, the RF coil forms an exterior surface of the incubator and an interior surface of the patient compartment;
- wherein the MRI system is configured to generate acoustic noise from a noise source during operation, the noise source being exterior of the patient compartment;
- wherein the receiver defines a bounded passage extending between an exterior of the patient compartment and an interior of the patient compartment, the passage including:
  - an entrance port opening from the exterior of the patient compartment into the receiver;
  - a first passage segment extending from the entrance port in a first direction;
  - a first reflective surface at an end of the first passage segment, the first reflective surface being orthogonal to the first passage segment;
  - a second passage segment joined to the first passage segment and extending in a second direction oriented at a right angle relative to the first direction;

a second reflective surface at an end of the second passage segment, the second reflective surface being orthogonal to the second passage segment;

a third passage segment joined to the second passage segment and extending in a third direction oriented at a right angle relative to the second direction; and an exit port opening from the third passage segment into the interior of the patient compartment;

wherein the first reflective surface and the second reflective surface are orthogonal to one another, and the first passage segment, the second passage segment, the first reflective surface, and the second reflective surface are structurally arranged such that acoustic waves entering through the entrance port and propagating along the first passage segment strike the first reflective surface, with a first portion of the acoustic waves reflected back toward the entrance port, and a second portion of the acoustic waves passing into the second passage segment and striking the second reflective surface, the second reflective surface reflecting the second portion back toward the first passage segment and away from the exit port;

whereby, by virtue of the structural arrangement, acoustic energy at the exit port is reduced relative to acoustic energy entering through the entrance port.

19. The incubator according to claim 18, wherein when the hood is engaged with the receiver, an exterior surface of the patient compartment is defined by both the hood and the RF coil.

20. The incubator according to claim 18, wherein when the hood is engaged with the receiver, the RF coil forms an exterior surface of the incubator and an interior surface of the patient compartment.

* * * * *